United States Patent [19]
Gwaltney

[11] Patent Number: 5,595,174
[45] Date of Patent: Jan. 21, 1997

[54] NASAL ADAPTOR, MASK, AND METHOD

[76] Inventor: Max R. Gwaltney, 1911 NW. 119 Ave., Pembroke Pines, Fla. 33026

[21] Appl. No.: 202,586

[22] Filed: Feb. 28, 1994

[51] Int. Cl.$^6$ .................................................. A62B 18/08
[52] U.S. Cl. .............................. 128/201.15; 128/201.13; 128/207.18
[58] Field of Search .................. 128/201.15, 201.13, 128/207.18

[56] References Cited

U.S. PATENT DOCUMENTS

| | | | |
|---|---|---|---|
| 396,936 | 1/1889 | Jennings | 128/207.18 |
| 603,021 | 4/1898 | Dight | 128/201.13 |
| 718,785 | 1/1903 | McNary | 128/207.18 |
| 759,152 | 5/1904 | Bennett | 128/207.18 |
| 1,125,542 | 1/1915 | Humphries | 128/207.18 |
| 1,362,766 | 12/1920 | McGargill | 128/206.11 |
| 1,443,820 | 1/1923 | Hudson | 128/207.18 |
| 2,062,325 | 12/1936 | Manson | 128/201.15 |
| 2,751,906 | 6/1956 | Irvine | 128/206.11 |
| 2,792,000 | 5/1957 | Richardson | 128/201.15 |
| 3,905,335 | 9/1975 | Kapp | 128/206.11 |
| 4,154,235 | 5/1979 | Warncke | 128/201.25 |
| 4,458,679 | 7/1984 | Ward | 128/201.13 |
| 4,478,215 | 10/1984 | Hanlon | 128/201.13 |
| 4,614,186 | 9/1986 | John | 128/201.25 |
| 4,683,869 | 8/1987 | Wilcox | 128/201.13 |
| 4,768,235 | 9/1988 | Webster | 128/201.29 |
| 4,782,832 | 11/1988 | Trimble et al. | 128/207.18 |
| 4,919,128 | 4/1990 | Kopala et al. | 128/207.18 |
| 4,996,983 | 3/1991 | AmRhein | 128/207.18 |
| 5,029,572 | 7/1991 | LeBlanc | 128/201.13 |
| 5,042,478 | 8/1991 | Kopala et al. | 128/207.18 |

*Primary Examiner*—Aaron J. Lewis
*Attorney, Agent, or Firm*—Dominik & Stein

[57] ABSTRACT

A nasal adapter and relatively fixed tube in which the inserts penetrate the nostrils, and a fixed tube diverts the inhaled and exhaled air laterally at a generally 90° angle to the angle of breathing out of the nostrils is disclosed. The invention looks to combining such an adapter with a mask in which the mask has a slit on one side in order to receive the pipe which is directed from the adapter and physically support the same along with the adapter and the nostrils to a comfortable position and insuring that the exhaling will be to the exterior of the mask. The method of the present invention looks to the steps of inserting a nasal adapter into the nostrils, diverting the air laterally from the breather, and encapsulating the head portion of the person wearing the nasal adapter in a cover or mask from which the eyeglasses of the wearer are permitted to view outside the mask.

6 Claims, 2 Drawing Sheets

NASAL ADAPTOR, MASK, AND METHOD

FIELD OF THE INVENTION

The present invention relates to a breathing device, and more particularly a breathing device which, when used with a mask, substantially eliminates the fogging of eyeglasses when worn by the user.

SUMMARY OF THE PRIOR ART various types of devices have been used for connecting the nostrils with breathing apparatus. Such are exemplified in U.S. Pat. Nos. 396,936; 603,021; 718,785; 759,152; 1,125,542; 1,443,820; 2,792,000; 4,782,832; 4,919,128; 4,996,983; and 5,042,478. These patents were all located in Class 128, various subclasses including 201.13; 207.18; and 201.15. The device of McNary shown in U.S. Pat. No. 718,785 is not intended for use with a mask and actually requires breathing through a window. The Bennett device of U.S. Pat. No. 759,152 breathes onto a device for administering anesthetic gases. As to more recently issued U.S. Pat. No. 5,042,478 to Kopala, et al, it is more like a snorkel than a breathing device. The same applies to Kopala, et al U.S. Pat. No. 4,919,128. The patent to Trimble, et al U.S. Pat. No. 4,782,832 relates to a head gear and breathing mask for discharging the air rearwardly from the head. The AmRhein U.S. Pat. No. 4,996,983 also relates to the use of reading gases and a breathing apparatus, but is specifically limited by its coupling to a filtration system. Richardson U.S. Pat. No. 2,792,000 is more a kin to a gas mask than a breathing apparatus and does not involve a mask. Hudson U.S. Pat. No. 1,443,820 involves a complex of filters and a breathing device but not necessarily employing a nasal adapter. U.S. Pat. No. 1,125,542 to Humphries similarly discloses a breathing device but it, along with Jennings U.S. Pat. No. 396,936 and Dight U.S. Pat. No. 603,021 are addressed to anything other than a mask.

When a hunter or skier or other user utilizes a mask, a cutout area is at the upper portion of the mask so that eyeglasses can protrude to a sufficient degree in order for the user to observe his prey and deliver a good shot or make it down the slopes. When the masked person breaths heavily, particularly at lower temperatures and lower humidities, steam will form quickly on the eye glasses and reduce the masked person's visibility. Even if the hunter should breath downwardly, the moisture in the air has a tendency to condense and then rise again fogging the glasses.

What is needed is a breathing apparatus which is comfortable to wear by the user with a mask, whether camouflaged or otherwise, which will conveniently lead away the exhaled air to the outside of the mask so that the eyeglass of the user is not fogged by the breathing. A similar application can be made to a hunter's mask or ski mask for a skier wearing glasses who wishes to breath and divert the entirety of the exhaled air outside of the mask to avoid steaming the eyeglass lenses. Other applications doubtless exist where breathing is done in a confined area normally with head gear utilized by the user.

SUMMARY OF THE INVENTION

The present invention stems from the development of a nasal adapter and relatively fixed tube in which the inserts penetrate the nostrils, and a fixed tube diverts the inhaled and exhaled air laterally at a generally 90° angle to the angle of breathing out of the nostrils. Another aspect of the invention looks to combining such an adapter with a mask in which the mask has a slit at either the right or left side in order to receive the pipe which is directed from the adapter and physically support the same along with the adapter and the nostrils to a comfortable position and insuring that the exhaling will be to the exterior of the mask. Finally, the method of the present invention looks to the steps of inserting a nasal adapter into the nostrils, diverting the air laterally from the breather, and encapsulating the head portion of the person wearing the cannula in a cover or mask from which the eyeglasses of the wearer are permitted to view outside the mask.

In view of the foregoing it is a principal object of the present invention to provide a nasal adapter which diverts the air from the breathing person to a point outside of any covering over the head to eliminate the fogging of eyeglasses.

Yet another object of the present invention is to provide a combination of the nasal adapter, diverting pipe, and head mask which when worn together permit the effective utilization of eyeglasses with the mask in climates and conditions where otherwise the mask would be fogged by the exhaling of the user.

Yet another object of the present invention looks to the provision of a nasal adapter, adaptable for a mask, in which the cost to the wearer is minimal compared to the freedom from fogging eyeglasses.

Finally but another object of the present invention is to provide a nasal adapter, breathing tube, and mask which is inherently comfortable in use for the wearer and can be worn for prolonged periods of time while either skiing, waiting game, or otherwise observing in the out-of-doors in such a fashion that even a bird watcher would find the mask and cannula combination comfortable.

BRIEF DESCRIPTION OF THE DRAWINGS

Further objects and advantages of the present invention will become apparent as the following description of an illustrative embodiment proceeds, in which.

DETAILED DESCRIPTION OF A PREFERRED EMBODIMENT

Figure 1:
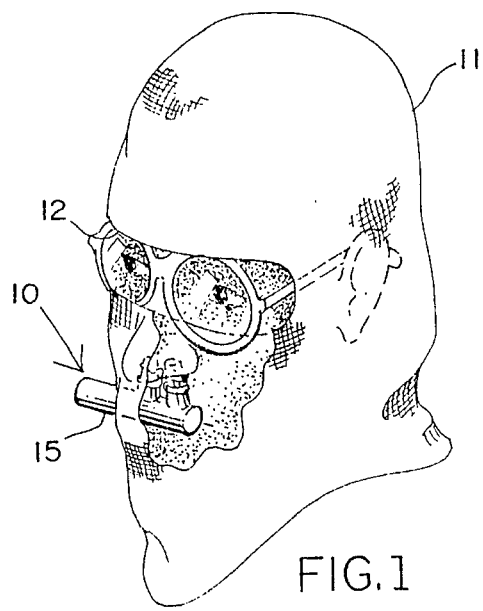
FIG. 1 is a perspective partially diagrammatic partially broken view of a user wearing eyeglasses utilizing the nasal adapter and mask combination of the present invention.
Figure 2:
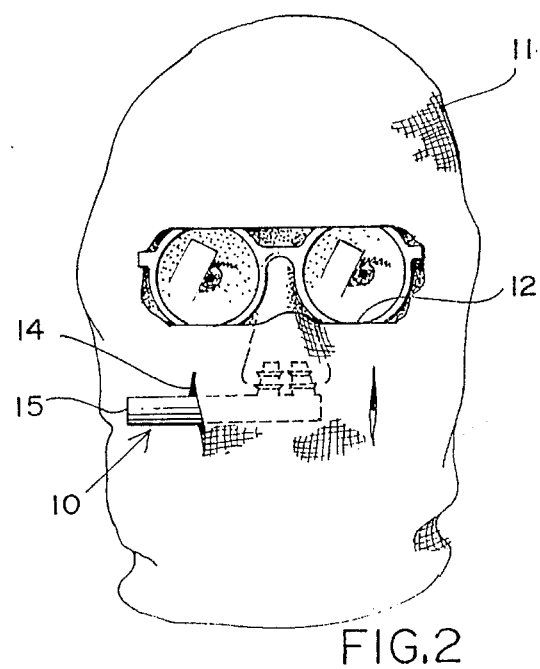
FIG. 2 is a front elevation of the subject user of FIG. 1.
Figure 3:
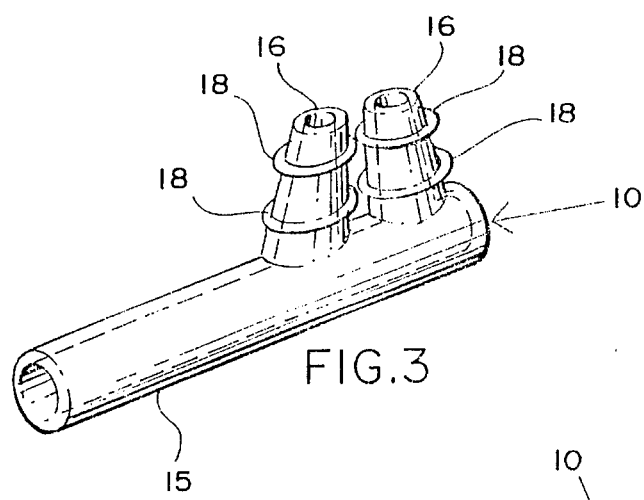
FIG. 3 is a perspective view of the nasal adapter portion of the subject device illustrating diagrammatically the phantom lines identifying the nose and nostrils of the user.
Figure 4:
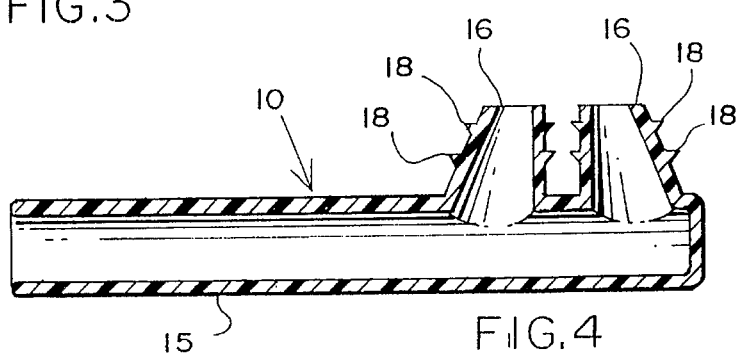
FIG. 4 is a longitudinal sectional view of the adapter shown in FIG. 3 in the same scale as FIG. 3 taken along 4—4 of FIG. 3 illustrating the interior portions of the adapter and lateral tube.
Figure 5:
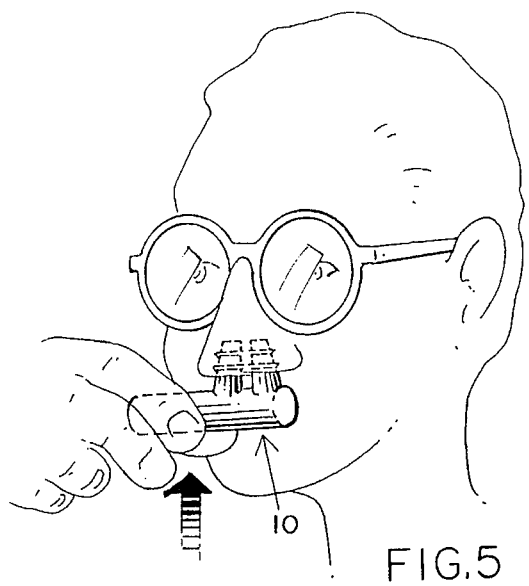
FIGS. 5, 6, and 7 are sequential views showing how the nasal adapter and tube of the illustrative embodiment are manipulated to position interiorly of the mask and then onto the person wearing the mask.
Figure 6:
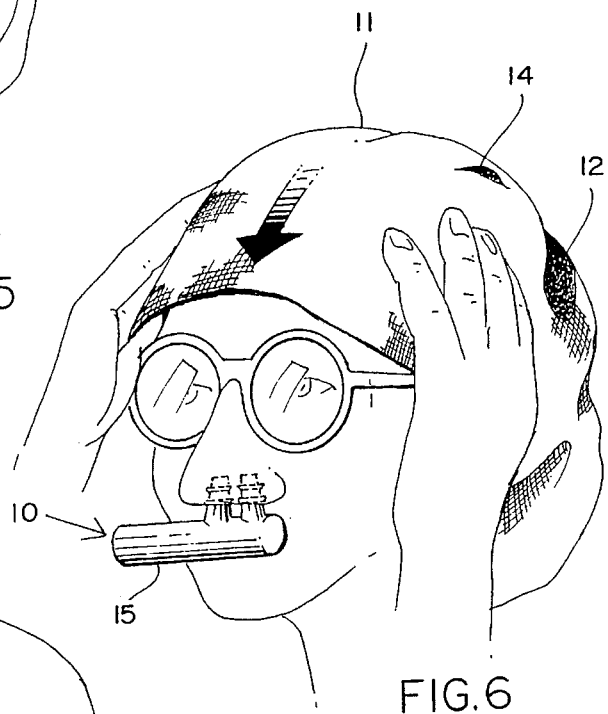
Figure 7:
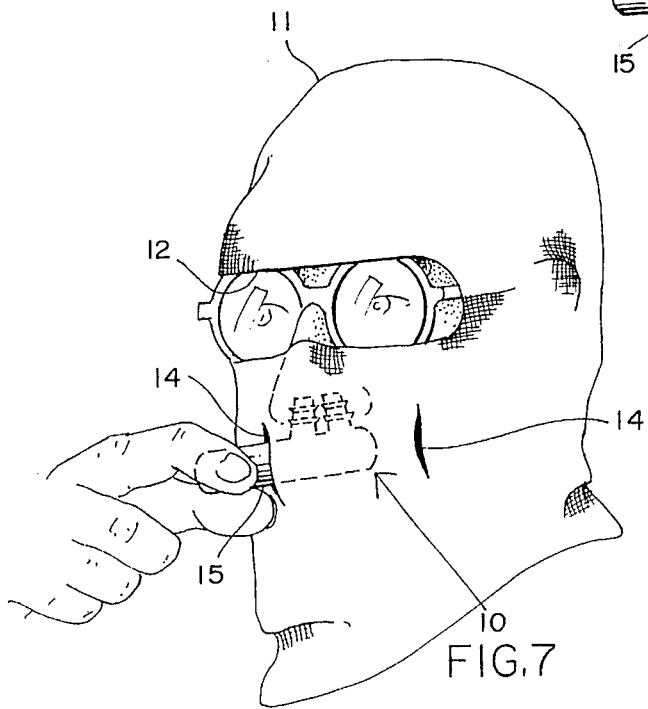

As noted in FIG. 1, the typical sportsman wearing eyeglasses has positioned a nasal adapter and tube assembly 10 in his nostrils, and positioned a mask 11 over his head so that the eyeglasses are free for a view through the mask eyeglass opening 12. A tube slot 14 is in one side of the mask is provided to receive the tube portion 15 of the nasal adapter and tube assembly 10 for use by the wearer. At this point it will be appreciated that a ski mask or other head covering could be employed by a person wearing eyeglasses who would obtain similar advantages. Those advantages will be better understood after a detailed description of the structure of the nasal adapter and tube assembly 10 proceed. More specifically, the subject nasal adapter 10 is shown in a perspective view in FIG. 3. The principal portions, namely the tube 15 and nostril inserts 16 are shown. In addition, the insert fins 18 appear as they encircle the nostril insert 16. Further details of the nostril inserts 16, their accompanying fins, and the tube 15 of the adapter assembly 10 appear in FIG. 4.

At this point, the tube 15 of the adapter assembly 10 is passed through the slot 14 of the mask 11 and the user is now ready to spend his time waiting for game, or whisking down the ski slope, or engaged in any other outdoor activity including bird watching in which fogging of the eyeglasses is to be avoided.

It will be understood that various changes in the details, materials and arrangements of parts which have been herein described and illustrated in order to explain the nature of the invention, may be made by those skilled in the art within the principle and scope of the invention as expressed in the appended claims.

I claim:

1. In combination, a nasal adapter and tube assembly and a head net having an eyeglass opening to accommodate eyeglasses for a person intending to wear the head net at the forward portion of said head net and port means at one side of the head net for receiving a portion of the nasal adapter and tube assembly, sand nasal adapter, head net, and tube assembly comprising, in combination, a head net with an eyeglass opening and a port at one side thereof, a nasal adapter body having laterally spaced nostril engaging inserts extending upwardly from a tube, a tube mounted in the lower portion of the nasal adapter body and extending laterally therefrom a distance to permit the tube to be moved outside the head net port, whereby warm moisture laden exhaled breath is diverted outwardly of the head net to avoid fogging eyeglasses of a head net wearer.

2. The nasal adapter and tube assembly of claim 1, in which said nasal adapter body has nostril engaging inserts which are frostoconically shaped.

3. In the nasal adapter and tube assembly of claim 2, said nostril engaging inserts having one or more circular fins extending laterally from the body of said inserts.

4. A nasal adapter and head net assembly comprising, in combination, an adapter tube having means for insertion into the nostrils of a user, said nasal adapter having a laterally disposed outlet port at the end of the tube, a head net having an uninterrupted eyeglass opening at a central portion thereof and a nasal adapter tube receiving opening on a lateral side thereof proportioned to receive the tube of the nasal adapter, whereby the nasal adapter and tube can be inserted in the head net and a user will breath air inwardly and outwardly which will find its ingress and egress from the side of the head net or a user may inhale through the mouth and exhale through the nose as a user may elect thereby diverting moist exhaled air outside the head net to avoid fogging eyeglasses of a user of the head net.

5. The nasal adapter of claim 4, in which said nasal adapters are frostoconically shaped.

6. In the nasal adapter of claim 4, said nostril engaging inserts having one or more circular fins extending laterally from the body of said inserts.

* * * * *